United States Patent
Rao et al.

(10) Patent No.: US 12,171,624 B1
(45) Date of Patent: Dec. 24, 2024

(54) AUTOMATIC GRINDING DRILL DEVICE FOR ORAL CARIES

(71) Applicant: SICHUAN UNIVERSITY, Sichuan (CN)

(72) Inventors: Guocheng Rao, Sichuan (CN); Weichang Chen, Sichuan (CN); Zitong Zeng, Sichuan (CN); Chan Yang, Sichuan (CN); Bo Zhang, Sichuan (CN); Yonggang Liang, Sichuan (CN); Nan Lin, Sichuan (CN); Xueyan Zhou, Sichuan (CN); Xuan Li, Sichuan (CN); Zhenwei Wen, Sichuan (CN); Tao Li, Sichuan (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/773,626

(22) Filed: Jul. 16, 2024

(30) Foreign Application Priority Data

Nov. 24, 2023 (CN) .......................... 202311581916.6

(51) Int. Cl.
*A61C 1/05* (2006.01)
*A61B 34/20* (2016.01)
(Continued)

(52) U.S. Cl.
CPC .............. *A61C 1/052* (2013.01); *A61B 34/20* (2016.02); *A61B 34/30* (2016.02); *A61C 1/08* (2013.01);
(Continued)

(58) Field of Classification Search
CPC ........... A61C 1/00; A61C 1/052; A61C 1/003; A61C 1/08; A61C 1/082; A61C 1/0007;
(Continued)

(56) References Cited

U.S. PATENT DOCUMENTS 9,554,872 B2 * 1/2017 Koubi .................. A61C 1/0007
10,052,171 B1 * 8/2018 Almalki ............. A61B 1/00091
(Continued)

FOREIGN PATENT DOCUMENTS

CN 104739528 A 7/2015
CN 104958118 A 10/2015
(Continued)

OTHER PUBLICATIONS

Search Report of counterpart Chinese Patent Application No. 202311581916.6 issued on Dec. 22, 2023.
(Continued)

*Primary Examiner* — Edward Moran

(57) ABSTRACT

The present invention relates to dental medical instruments, and specifically discloses an automatic grinding drill device for oral caries, including a mounting frame. Two retainers are arranged on the mounting frame, the bottom of the mounting frame is connected with a support plate through drive assemblies, a drill bit assembly is arranged at the bottom of the support plate, and a visual recognition module is also arranged on the support plate. The present invention has the advantage that the retainers keep a real-time relative static state with teeth of a patient during use, needing no frequent correction, so that operation steps are simplified.

6 Claims, 4 Drawing Sheets

(51) Int. Cl.
*A61B 34/30* (2016.01)
*A61C 1/08* (2006.01)
*A61C 1/14* (2006.01)

(52) U.S. Cl.
CPC ........ *A61C 1/14* (2013.01); *A61B 2034/2065* (2016.02); *A61B 2034/302* (2016.02)

(58) Field of Classification Search
CPC ........... A61C 3/02; A61B 34/23; A61B 34/30; A61B 17/176
See application file for complete search history.

(56) References Cited

U.S. PATENT DOCUMENTS

| | | | | |
|---|---|---|---|---|
| 11,337,773 | B2* | 5/2022 | Habeb | A61C 1/082 |
| 2020/0054421 | A1* | 2/2020 | Mozes | A61B 5/0088 |
| 2020/0315754 | A1* | 10/2020 | Ciriello | A61B 90/14 |
| 2021/0228317 | A1* | 7/2021 | Ciriello | A61C 1/082 |
| 2022/0061940 | A1 | 3/2022 | Cordasco | |
| 2022/0142736 | A1* | 5/2022 | Kim | A61C 1/082 |

FOREIGN PATENT DOCUMENTS

| | | | |
|---|---|---|---|
| CN | 107496048 | A | 12/2017 |
| CN | 108742887 | A | 11/2018 |
| CN | 208784944 | U | 4/2019 |
| CN | 208958355 | U | 6/2019 |
| CN | 110520074 | A | 11/2019 |
| CN | 110811873 | A | 2/2020 |
| CN | 211094874 | U | 7/2020 |
| CN | 112384166 | A | 2/2021 |
| CN | 113384374 | A | 9/2021 |
| CN | 216221745 | U | 4/2022 |
| CN | 115153925 | A | 10/2022 |
| CN | 115211987 | A | 10/2022 |
| CN | 115721424 | A | 3/2023 |
| CN | 116019582 | A | 4/2023 |
| CN | 219230177 | U | 6/2023 |
| CN | 116459010 | A | 7/2023 |
| CN | 116549144 | A | 8/2023 |
| DE | 102008063695 | A1 | 6/2010 |
| EP | 3834769 | A1 | 6/2021 |
| JP | 2006212244 | A | 8/2006 |
| KR | 20130123192 | A | 11/2013 |
| KR | 101653494 | B1 | 9/2016 |
| KR | 20190115342 | A | 10/2019 |
| KR | 102073281 | B1 | 3/2020 |
| WO | 2017100828 | A1 | 6/2017 |
| WO | 2020048545 | A1 | 3/2020 |
| WO | 2021015599 | A1 | 1/2021 |

OTHER PUBLICATIONS

Notice of Allowance of counterpart Chinese Patent Application No. 202311581916.6 issued on Dec. 27, 2023.

Run-Cheng Wang et al., Application of artificial intelligence in dental implant, Chin J Prosthodont, Mar. 2022, pp. 81-85, vol. 23, No. 2.

Qin Wu et al., Current research and application situation of robot in stomatology, International Journal of Stomatology, Sep. 2018, pp. 615-620, vol. 45. No. 5.

Zhenxing Tang et al., Relative anchorage loss under reciprocal anchorage in mandibular premolar extraction cases treated with clear aligners, Angle Orthodontist, 2023, pp. 375-381, vol. 93, No. 4.

Fusong Yuan et al., A preliminary study on a tooth preparation robot, Advances in Applied Ceramics, 2020, pp. 332-337, vol. 119, Nos. 5-6.

* cited by examiner

AUTOMATIC GRINDING DRILL DEVICE FOR ORAL CARIES

CROSS REFERENCE TO RELATED APPLICATIONS

The present application claims the benefit of Chinese Patent Application No. 202311581916.6 filed on Nov. 24, 2023, the contents of which are incorporated herein by reference in their entirety.

TECHNICAL FIELD

The present invention relates to dental medical instruments, and in particular, to an automatic grinding drill device for oral caries.

BACKGROUND

At present, the traditional operating procedure for teeth decay in the oral endodontics department is still to manually remove carious tissues-acid-etch the tooth surface-bond the restorative material. The removal of carious tissues is the most time-consuming part of the process and is also the key to determining the treatment effect. During the manual removal of carious tissues, the doctor needs to confirm the amount of tooth tissues removed and polish the cavity bottom and walls as smooth as possible. Traditional treatment methods have very different treatment effects among different doctors due to the influence of uncertain factors such as small space and lighting in the oral cavity, tooth color, doctor's condition and experience, and on-the-spot judgment ability. Difficult operating environment in the oral cavity often makes it impossible for the quality of cavity preparation to meet all standards. The risk of pulp penetration during manual operation also poses a great medical safety hazard, seriously affecting the quality of tooth preparation. Currently, dental departments such as implantology and prosthodontics have designed and manufactured oral robots to assist doctors in performing clinical operations such as dental implant and abutment preparation. However, the oral robots are all currently fixed on dental chairs or on the ground, occupying a large space and unable to remain relatively still with the patient at the same time. Once the patient moves during the examination or treatment, readjustment must be performed to maintain the original position relationship. These problems limit the popularity of automated oral treatment robots and make the treatment process complicated and redundant. Therefore, developing an automated caries preparation robot that can remain relatively still has become a feasible solution today to improve the effectiveness of caries treatment.

SUMMARY

An objective of the present invention is to overcome the disadvantages of the prior art and provide an automatic grinding drill device for oral caries.

The objective of the present invention is achieved through the following technical solution: an automatic grinding drill device for oral caries includes a mounting frame, where two retainers are arranged on the mounting frame, the bottom of the mounting frame is connected with a support plate through drive assemblies, a drill bit assembly is arranged at the bottom of the support plate, and a visual recognition module is also arranged on the support plate.

Specifically, each of the drive assemblies includes a connecting ear, a drive motor, and a connecting rod, where the drive motors are fixedly arranged on the connecting ears, output ends of the drive motors are connected with rotating frames, one ends of the connecting rods are hinged to the rotating frames, and the other ends thereof are each hinged with universal joints that are hinged to the support plate Specifically, three drive assemblies are provided and distributed in a triangular shape.

Specifically, the drill bit assembly includes a column, a second drive motor is arranged on the column, a rotary frame is arranged at an output end of the second drive motor, a third drive motor is arranged on the rotary frame, and an air drill is arranged at an output end of the third drive motor.

Specifically, the air drill includes a housing and a rotating shaft, where the rotating shaft is rotatably arranged in the housing, fan blades are arranged on the rotating shaft, one end of the rotating shaft extends out of the housing and is connected with a drill bit, an air inlet channel is arranged in the housing, an air outlet end of the air inlet channel is arranged in a radial direction of the housing, the air inlet channel is connected with an air inlet pipeline, and the housing is communicated with an air outlet pipe.

Specifically, the diameter of the air outlet pipe is less than that of the air inlet channel.

Specifically, the visual recognition module includes a fixing clamp and a camera, where the fixing clamp is arranged on the support plate, the camera is fixed on the fixing clamp, a light-transmitting hole is defined in the support plate, the camera is located above the light-transmitting hole, and fill lights are arranged around the camera.

Specifically, a slide groove is arranged on the periphery of the bottom of the support plate, a slider that is slidably arranged in the slide groove is arranged on an upper end of the column, a locking groove is arranged on a side wall of the support plate to communicate the slide groove, a lock screw is arranged on the slider, and the lock screw cooperates with the locking groove to lock the slider in the slide groove.

Specifically, the bottom of the housing is provided with water outlet holes and air outlet holes around the drill bit, and the water outlet holes are communicated with a water inlet pipe.

A method for cutting using an automatic grinding drill device for oral caries includes the following steps:

S1. Retainers are mounted in a patient's oral cavity, the patient's oral cavity is propped open by the retainers, and the retainers are fixed in the oral cavity through the patient's natural bite force to be positioned with the teeth;

S2. Image information of a tooth is collected through a camera and is uploaded to an artificial intelligence image recognition system, and the artificial intelligence image recognition system analyzes and obtains an edge contour and a carious part of the tooth, and plans cutting trajectory and range;

S3. A control system controls three drive motors to rotate and drive a support plate to drive an air drill to a preset position, supplies air to an air inlet channel through an air inlet pipeline to drive a drill bit to rotate, and drives the drill bit to move to cut the tooth by controlling the drive motors, a second drive motor and a third drive motor. While cutting, the control system supplies water through a water inlet pipe, and water outlet holes spray water to take away the heat generated by the cutting. While spraying water, the air in a housing is sprayed from air outlet holes to blow away the cut debris;

S4. As the drill bit continues to descend, the control system stops powering the drive motors, the second drive motor and the third drive motor when the drill bit descends 1 mm. At this time, the water outlet holes and the air outlet holes respectively spray air and water to clean the tooth surface. The camera then collects the image information of the tooth again and uploads the image information to the artificial intelligence image recognition system for subsequent cutting planning. After that, S3 is repeated until the cutting is completed. By means of multiple recognitions and cuttings, the bad part can be cut cleanly.

The present invention has the following advantages:

The caries removal device of the present invention can cooperate with an artificial intelligence image recognition system to automatically determine the edge of a carious part and plan a cutting position, so that fast, real-time and safe preparation of carious abutment is achieved, and the smoothness of cavity bottom and walls can be ensured while controlling the cutting depth, thereby improving the treatment effect while increasing the tooth preparation efficiency.

The retainers of the present invention keep a real-time relative static state with teeth of a patient during use, needing no frequent correction, so that operation steps are simplified.

1—retainer, 2—connecting ear, 4—column, 5—third drive motor, 6—housing, 7—drill bit, 8—rotary frame, 9—support plate, 10—universal joint, 11—connecting rod, 12—drive motor, 13—rotating frame, 14—mounting frame, 15—fill light, 16—camera, 17—fixing clamp, 18—second drive motor, 19—slider, 20—air inlet pipeline, 21—air outlet pipe, 22—water inlet pipe, 23—lock screw, 24—air inlet channel, 25—rotating shaft, 26—fan blade, 27—slide groove, 28—locking groove, 29—light-transmitting hole.

DETAILED DESCRIPTION

The present invention is further described below in conjunction with the accompanying drawings, but the scope of protection of the present invention is not limited to the following.

Figure 1:
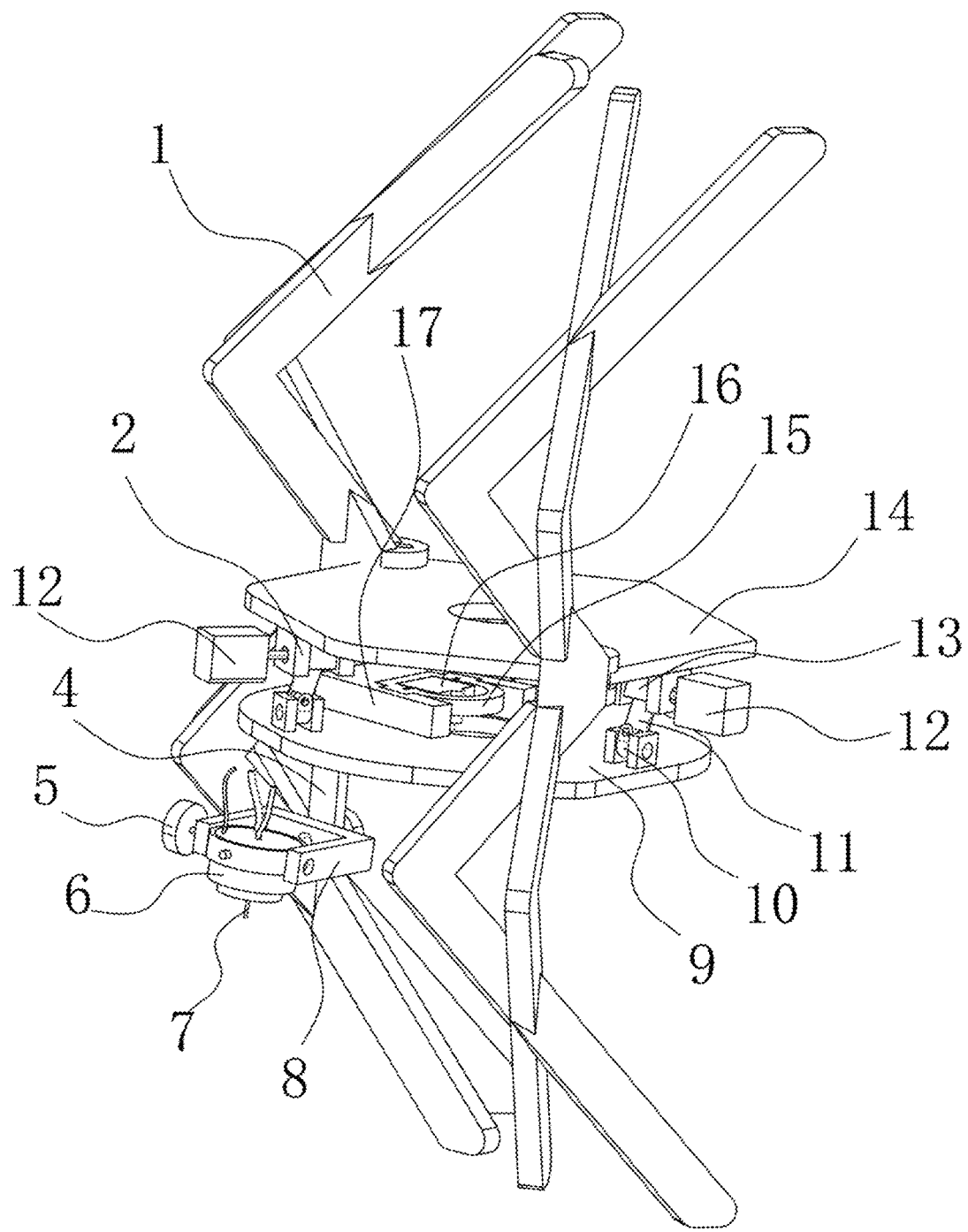
FIG. 1 is a schematic diagram (I) of an overall structure of a caries removal device of the present invention.
Figure 2:
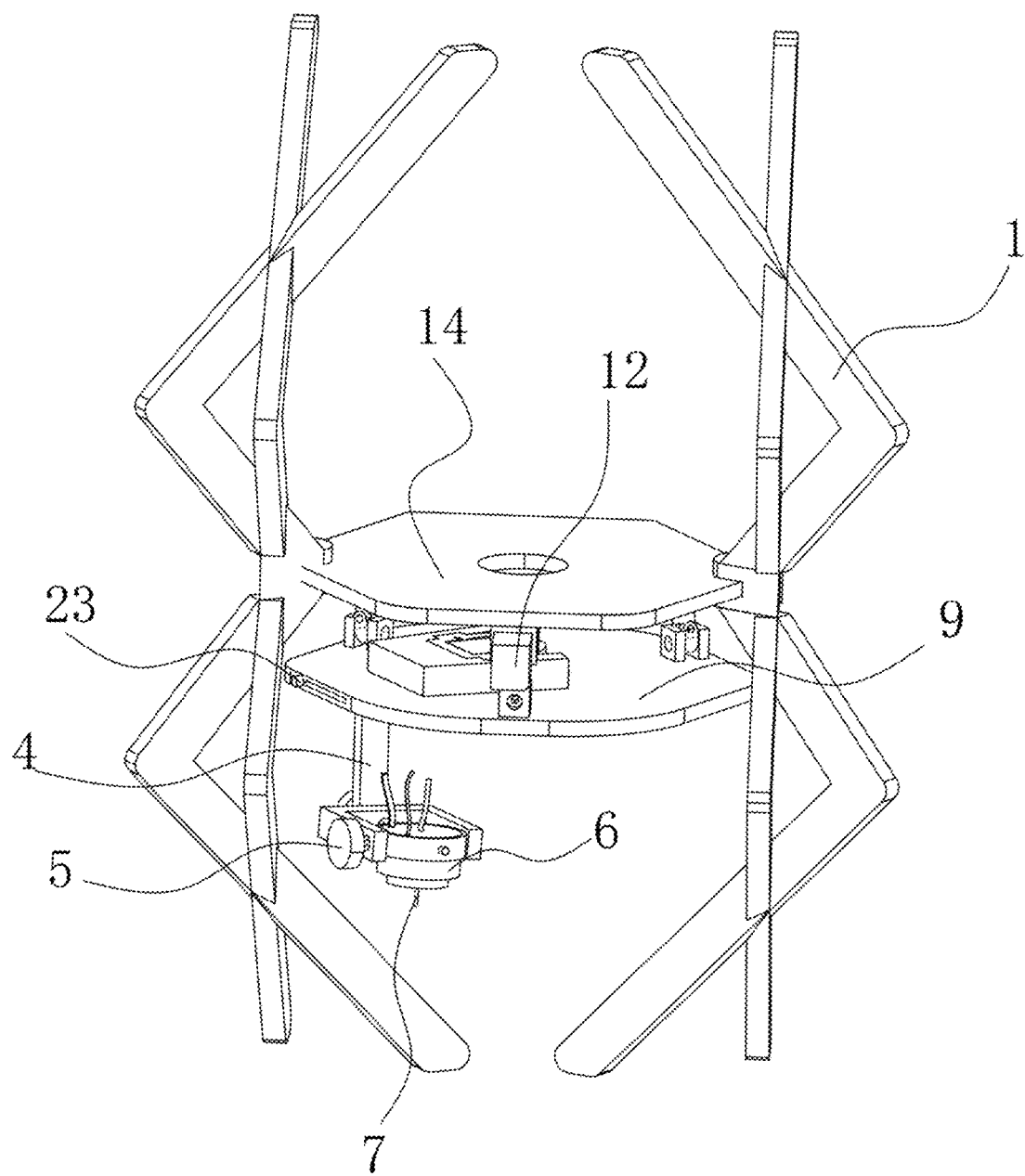
FIG. 2 is a schematic diagram (II) of the overall structure of the caries removal device of the present invention.
Figure 3:
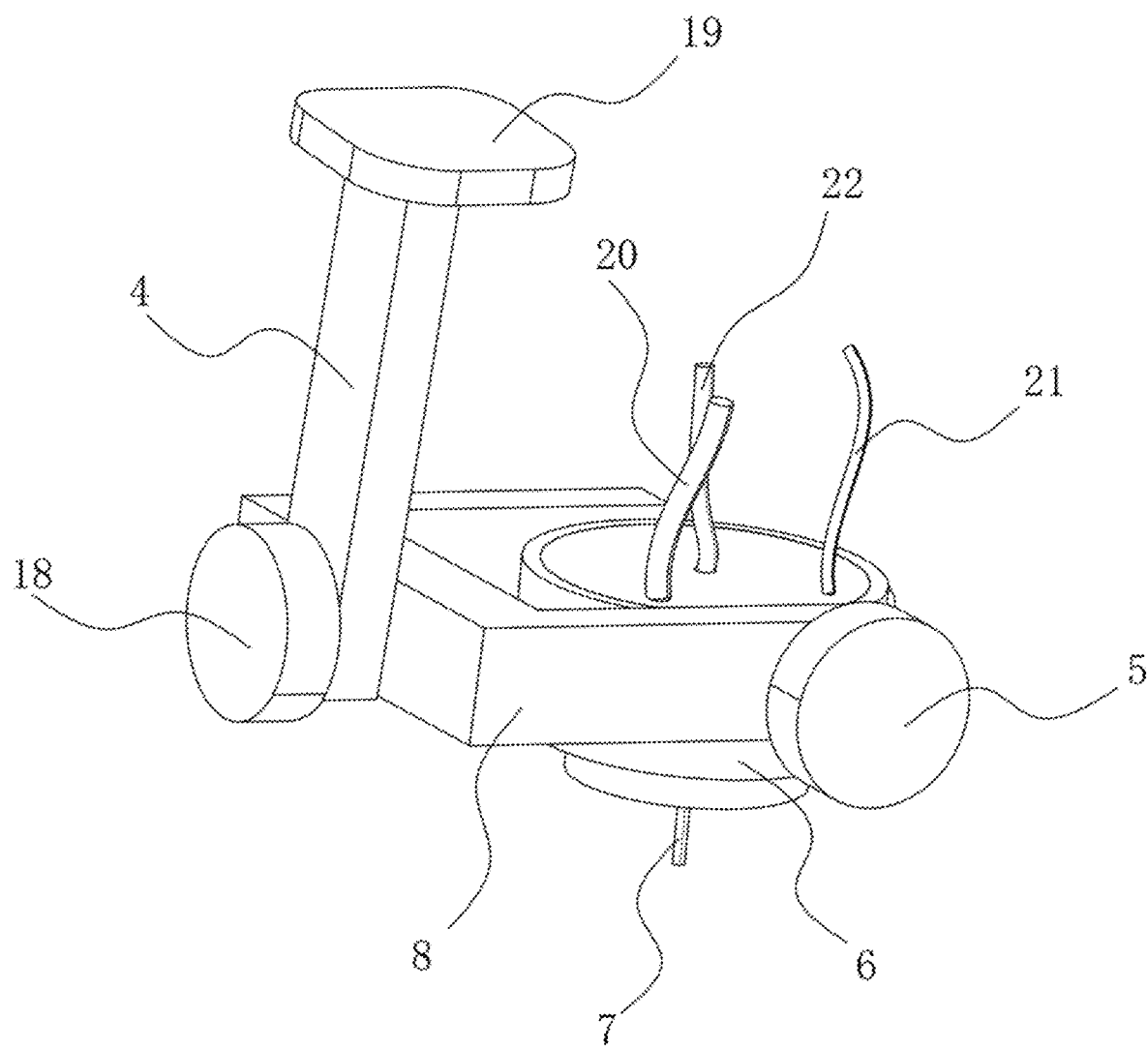
FIG. 3 is a schematic structural diagram of a drill bit assembly of the present invention.
Figure 4:
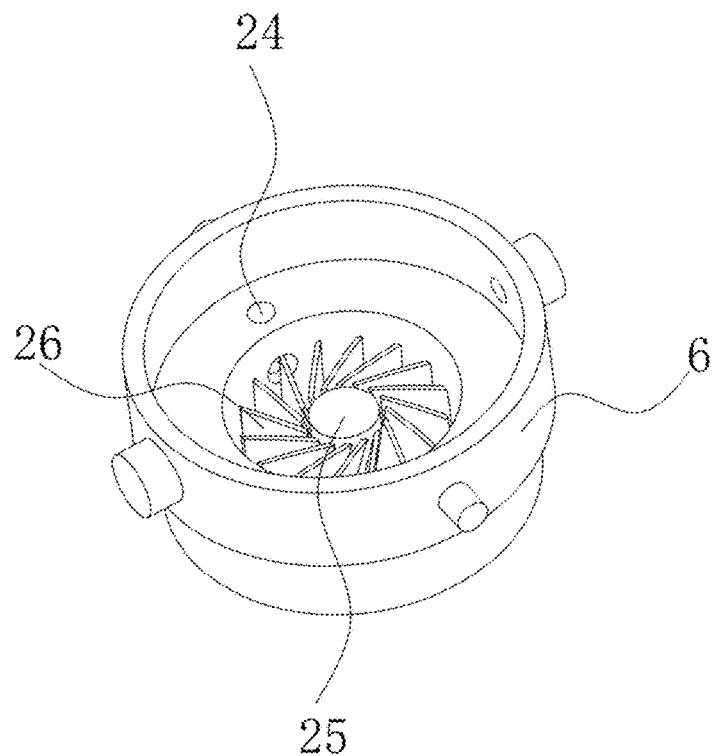
FIG. 4 is a schematic diagram of an internal structure of a housing of the present invention.
Figure 5:
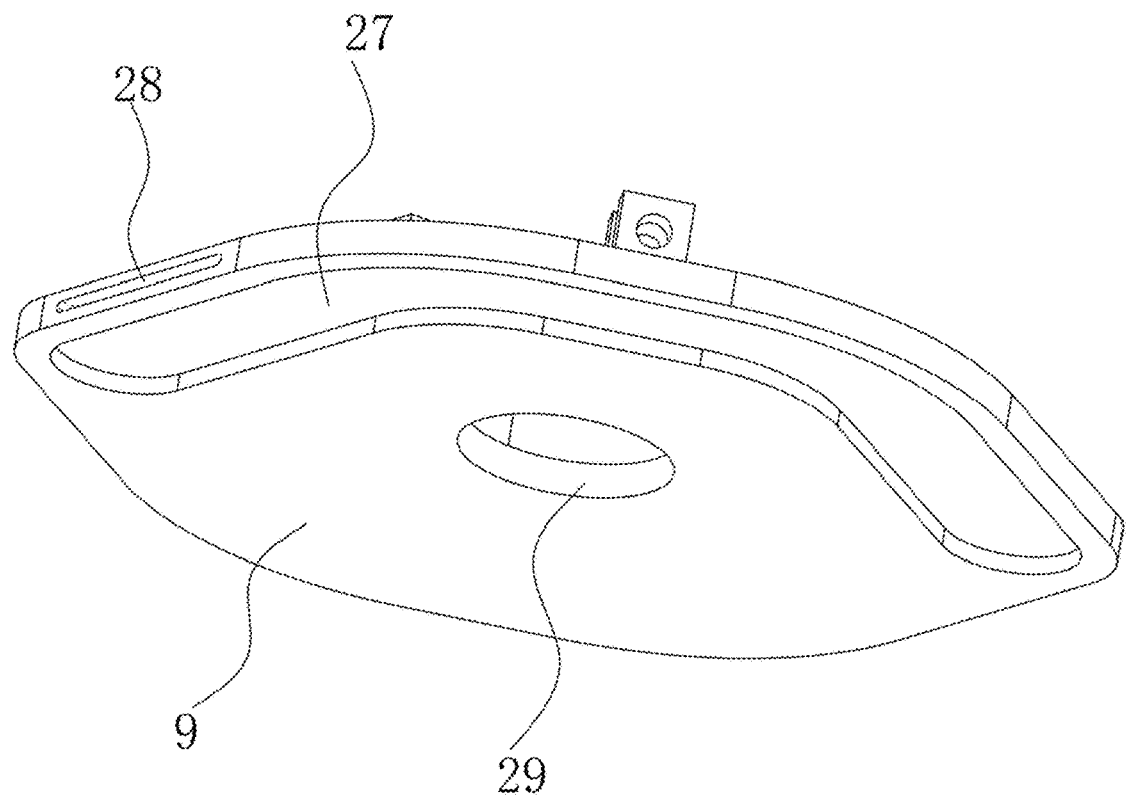
FIG. 5 is a schematic diagram of a bottom structure of a support plate of the present invention.

As shown in FIGS. 1 to 5, an automatic grinding drill device for oral caries includes a mounting frame 14. Two retainers 1 are arranged on the mounting frame 14. The bottom of the mounting frame 14 is connected with a support plate 9 through drive assemblies. A drill bit assembly is arranged at the bottom of the support plate 9. A visual recognition module is also arranged on the support plate 9. In this embodiment, a mounting frame 14 is provided for mounting two retainers 1. The mounting frame 14 is of a flat plate structure, and the two retainers 1 are arranged outside the mounting frame 14. When in use, the two retainers 1 are put in a patient's oral cavity, and a stable relationship between the retainers and the patient's dentition is achieved through the patient's natural biting force, such that the caries removal device and the patient's teeth can remain relatively still, and that when the patient's head moves, the caries removal device will not move relative to the teeth, which is more convenient to use. The support plate 9 is arranged at the bottom of the mounting frame 14 through the drive assemblies, and the drill bit assembly and the visual recognition module are arranged on the support plate 9. Before the treatment, the visual recognition module automatically collects images of caries and uploads the images to an analysis system. The system comprehensively analyzes and obtains an edge contour and a carious part of the tooth, and automatically plans cutting trajectory and range to prepare for subsequent automated cutting. After the drive assemblies drive the support plate 9 to move to drive the drill bit assembly to a preset position, the cutting starts. The drill bit assembly is controlled by a disconnecting circuit, with the disconnecting length controlled at 1 mm. When the cutting starts, the drill bit assembly continues to descend with continuous cutting. The circuit automatically disconnects and stops power supply when the drill bit assembly descends to 1 mm. Then, the visual recognition module automatically collects images again and uploads the images to the analysis system for subsequent cutting planning. By means of multiple cuttings, the removal of carious tissues can be completed.

In this embodiment, three drive assemblies are provided and distributed in a triangular shape. Each of the drive assemblies includes a connecting car 2, a drive motor 12, and a connecting rod 11. The drive motors 12 are fixedly arranged on the connecting cars 2, and output ends of the drive motors 12 are connected with rotating frames 13. One ends of the connecting rods 11 are hinged to the rotating frames 13, and the other ends thereof are each hinged with universal joints 10 that are hinged to the support plate 9. In this embodiment, by controlling the drive motors 12 of the three drive assemblies, the drive motors 12 rotate to drive the rotating frames 13 to rotate, and the rotating frames 13 rotate to drive the connecting rods 11 to move. Since one ends of the connecting rods 11 are hinged to the support plate 9 through the universal joints 10, the three drive motors 12 can cooperate to drive the support plate 9 to move up and down and move parallel to each other, so that the drill bit assembly can be moved to the preset position.

Further, the drill bit assembly includes a column 4. A second drive motor 18 is arranged on the column 4, and a rotary frame 8 is arranged at an output end of the second drive motor 18. A third drive motor 5 is arranged on the rotary frame 8, and an air drill is arranged at an output end of the third drive motor 5. Due to irregular shape of the caries, the drill bit assembly needs to be controlled so as to adapt to the removal of irregular caries. The column 4 is fixed to the bottom of the support plate 9, and a second drive motor 18 is fixed to the bottom of the column 4. The rotary frame 8 is fixed to the output end of the second drive motor 18, and the third drive motor 5 is fixed on the rotary frame 8. The air drill is arranged at the output end of the third drive motor 5, and the output shaft of the second drive motor 18 is perpendicular to that of the third drive motor 5. In this way, by controlling the second drive motor 18 and the third drive motor 5, the air drill can be driven to tilt and can be adjusted to the optimal caries grinding angle.

In this embodiment, the air drill includes a housing 6 and a rotating shaft 25. The rotating shaft 25 is rotatably arranged in the housing 6, and fan blades 26 are arranged on the rotating shaft 25. One end of the rotating shaft 25 extends out of the housing 6 and is connected with a drill bit 7. An air inlet channel 24 is arranged in the housing 6, and an air outlet end of the air inlet channel 24 is arranged in a radial direction of the housing 6. The air inlet channel 24 is connected with an air inlet pipeline 20, and the housing 6 is communicated with an air outlet pipe 21. In this embodiment, the housing 6 is fixed to the output end of the third drive motor 5, and the rotating shaft 25 is rotatably arranged in the housing 6. The rotating shaft 25 can be driven by high-pressure air to reach a speed of 20,000 r/min for caries cutting. Specifically, by providing a plurality of fan blades 26 on the outer wall of the rotating shaft 25, an air source is connected through the air inlet pipeline 20, and the high-pressure air enters the air inlet pipeline 20 and then enters the housing 6 through the air inlet channel 24 to blow the fan blades 26, so as to drive the rotating shaft 25 to rotate. The rotation of the rotating shaft 25 can drive the drill bit 7 to cut the caries, and the air in the housing 6 is discharged through the air outlet pipe 21.

In this embodiment, the diameter of the air outlet pipe 21 is less than that of the air inlet channel 24, so that an air pressure difference can be formed in the housing 6 to drive the rotating shaft 25 to rotate.

In this embodiment, the visual recognition module includes a fixing clamp 17 and a camera 16. The fixing clamp 17 is arranged on the support plate 9, and the camera 16 is fixed on the fixing clamp 17. A light-transmitting hole 29 is defined in the support plate 9, and the camera 16 is located above the light-transmitting hole 29. Fill lights 15 are arranged around the camera 16. In this embodiment, the fixing clamp 17 is arranged on the support plate 9 for fixing the camera 16. The camera 16 collects images of the caries through the light-transmitting hole 29 defined in the support plate 9. In order to make the collected images clear, the fill lights 15 are arranged around the camera 16 on the fixing clamp 17 for illumination in this embodiment.

In this embodiment, a slide groove 27 is arranged on the periphery of the bottom of the support plate 9. A slider 19 that is slidably arranged in the slide groove 27 is arranged on an upper end of the column 4. A locking groove 28 is arranged on a side wall of the support plate 9 to communicate the slide groove 27. A lock screw 23 is arranged on the slider 19, and the lock screw 23 cooperates with the locking groove 28 to lock the slider 19 in the slide groove 27. In order to remove teeth in different positions in this embodiment, the slide groove 27 is arranged at the bottom of the support plate 9, and the slider 19 that is slidably arranged in the slide groove 27 is arranged on the top of the column 4. By moving the slider 19 in the slide groove 27, the position of the air drill can be adjusted to adapt to teeth in different positions. After the slider 19 is moved into place, the lock screw 23 can be tightened to fix the slider 19 on the support plate 9, thereby achieving the purpose of adjustment. The adjusted position of the air drill is positioned by the camera 16.

In this embodiment, the bottom of the housing 6 is provided with water outlet holes and air outlet holes around the drill bit 7, and the water outlet holes are communicated with a water inlet pipe 22. Since high temperature is generated when grinding caries, the water inlet pipe 22 is needed to spray and cool down the caries part.

A method for cutting using an automatic grinding drill device for oral caries includes the following steps:

S1. Retainers 1 are mounted in a patient's oral cavity, the patient's oral cavity is propped open by the retainers 1, and the retainers 1 are fixed in the oral cavity through the patient's natural bite force to be positioned with the teeth;

S2. Image information of a tooth is collected through a camera 16 and is uploaded to an artificial intelligence image recognition system, and the artificial intelligence image recognition system analyzes and obtains an edge contour and a carious part of the tooth, and plans cutting trajectory and range;

S3. A control system controls three drive motors 12 to rotate and drive a support plate 9 to drive an air drill to a preset position, supplies air to an air inlet channel 24 through an air inlet pipeline 20 to drive a drill bit 7 to rotate, and drives the drill bit 7 to move to cut the tooth by controlling the drive motors 12, a second drive motor 18 and a third drive motor 5. While cutting, the control system supplies water through a water inlet pipe 22, and water outlet holes spray water to take away the heat generated by the cutting. While spraying water, the air in a housing 6 is sprayed from air outlet holes to blow away the cut debris;

S4. As the drill bit 7 continues to descend, the control system stops powering the drive motors 12, the second drive motor 18 and the third drive motor 5 when the drill bit 7 descends 1 mm. At this time, the water outlet holes and the air outlet holes respectively spray air and water to clean the tooth surface. The camera 16 then collects the image information of the tooth again and uploads the image information to the artificial intelligence image recognition system for subsequent cutting planning. After that, S3 is repeated until the cutting is completed. By means of multiple recognitions and cuttings, the bad part can be kept to be cut cleanly.

In S2, the collected images are analyzed by the artificial intelligence image recognition system to position the drill bit 7.

What is claimed is:

1. An automatic grinding drill device for oral caries, characterized in comprising a mounting frame, wherein two retainers are arranged on the mounting frame, and when in use, the two retainers are put in a patient's oral cavity such that a stable relationship between the retainers and the patient's dentition is achieved through the patient's natural biting force; the bottom of the mounting frame is connected with a support plate through drive assemblies; a drill bit assembly is arranged at the bottom of the support plate; a visual recognition module is also arranged on the support plate; the drill bit assembly comprises a column that is fixed to the bottom of the support plate; a second drive motor is arranged on the column, and a rotary frame is arranged at an output end of the second drive motor; a third drive motor is arranged on the rotary frame, and an air drill is arranged at an output end of the third drive motor; an output shaft of the second drive motor is perpendicular to that of the third drive motor; each of the drive assemblies comprises a connecting car, a drive motor, and a connecting rod; the drive motors are fixedly arranged on the connecting cars, and output ends of the drive motors are connected with rotating frames; one ends of the connecting rods are hinged to the rotating frames, and the other ends thereof are each hinged with universal joints that are hinged to the support plate; three drive assemblies are provided and distributed in a triangular shape.

2. An automatic grinding drill device for oral caries according to claim 1, characterized in that the air drill comprises a housing and a rotating shaft, wherein the rotating shaft is rotatably arranged in the housing, fan blades are arranged on the rotating shaft, one end of the rotating shaft extends out of the housing and is connected with a drill bit, an air inlet channel is arranged in the housing, an air outlet end of the air inlet channel is arranged in a radial direction of the housing, the air inlet channel is connected with an air inlet pipeline, and the housing is communicated with an air outlet pipe.

3. An automatic grinding drill device for oral caries according to claim 2, characterized in that the diameter of the air outlet pipe is less than that of the air inlet channel.

4. An automatic grinding drill device for oral caries according to claim 1, characterized in that the visual recognition module comprises a fixing clamp and a camera, wherein the fixing clamp is arranged on the support plate, the camera is fixed on the fixing clamp, a light-transmitting hole is defined in the support plate, the camera is located above the light-transmitting hole, and fill lights are arranged around the camera.

5. An automatic grinding drill device for oral caries according to claim 2, characterized in that a slide groove is arranged on the periphery of the bottom of the support plate, a slider that is slidably arranged in the slide groove is arranged on an upper end of the column, a locking groove is arranged on a side wall of the support plate to communicate the slide groove, a lock screw is arranged on the slider, and the lock screw cooperates with the locking groove to lock the slider in the slide groove.

6. An automatic grinding drill device for oral caries according to claim 2, characterized in that the bottom of the housing is provided with water outlet holes and air outlet holes around the drill bit, and the water outlet holes are communicated with a water inlet pipe.

* * * * *